US012564474B2

(12) United States Patent
Gonenc et al.

(10) Patent No.: US 12,564,474 B2
(45) Date of Patent: Mar. 3, 2026

(54) MOUNTING KIT FOR A SURGICAL ROBOTIC SYSTEM

(71) Applicant: Verb Surgical Inc., Santa Clara, CA (US)

(72) Inventors: Berk Gonenc, San Jose, CA (US); Benjamin Alan Sanker, San Jose, CA (US); Rose Huang, Quincy, MA (US)

(73) Assignee: Auris Health, Inc., Santa Clara, CA (US)

( * ) Notice: Subject to any disclaimer, the term of this patent is extended or adjusted under 35 U.S.C. 154(b) by 296 days.

(21) Appl. No.: 18/497,838

(22) Filed: Oct. 30, 2023

(65) Prior Publication Data

US 2025/0134620 A1     May 1, 2025

(51) Int. Cl.
| | |
|---|---|
| *A61B 90/50* | (2016.01) |
| *A61B 34/37* | (2016.01) |
| *A61B 50/13* | (2016.01) |
| *A61B 34/30* | (2016.01) |

(52) U.S. Cl.
CPC .............. *A61B 90/50* (2016.02); *A61B 34/37* (2016.02); *A61B 50/13* (2016.02); *A61B 2034/302* (2016.02)

(58) Field of Classification Search
None
See application file for complete search history.

(56) References Cited

U.S. PATENT DOCUMENTS

| | | | |
|---|---|---|---|
| 1,092,092 A | 3/1914 | Campbell | |
| 6,209,832 B1* | 4/2001 | Yamazaki | G01C 15/006 |
| | | | 248/231.71 |
| 2007/0119274 A1* | 5/2007 | Devengenzo | A61B 34/30 |
| | | | 74/490.01 |
| 2012/0025046 A1 | 2/2012 | Yen | |
| 2021/0007827 A1* | 1/2021 | Roussel | A61B 90/57 |
| 2022/0096120 A1* | 3/2022 | Bajo | A61B 17/3421 |
| 2022/0226049 A1* | 7/2022 | Scheib | A61G 13/04 |
| 2022/0226052 A1* | 7/2022 | Johnson | A61B 34/30 |
| 2025/0275830 A1* | 9/2025 | Abbott | A61B 90/57 |

OTHER PUBLICATIONS

VIVO; "VESA Quick Release Adapter;" received from https://vivo-us.com/products/stand-vad2; Jun. 30, 2013; 5 pgs.

* cited by examiner

*Primary Examiner* — Steven M Marsh
(74) *Attorney, Agent, or Firm* — Aikin & Gallant, LLP

(57) ABSTRACT

A bracket assembly for a surgical robotic system, the bracket assembly comprising: a bracket having a first side defining a mounting interface and a second side defining an out of plane portion dimensioned for insertion within a cable opening of an auxiliary video cart; and a bracket securing member having an engaging member dimensioned to slidably engage the out of plane portion and a plate dimensioned to support the engaging member and secure the bracket to the auxiliary video cart.

20 Claims, 9 Drawing Sheets

MOUNTING KIT FOR A SURGICAL ROBOTIC SYSTEM

TECHNICAL FIELD

This disclosure relates generally to the field of robotic surgery and, more particularly, to a mounting assembly or kit for mounting an auxiliary device to a support structure of a surgical robotic system using an existing opening of the support structure.

BACKGROUND

Minimally-invasive surgery (MIS), such as laparoscopic surgery, involves techniques intended to reduce tissue damage during a surgical procedure. For example, laparoscopic procedures typically involve creating a number of small incisions in the patient (e.g., in the abdomen), and introducing one or more tools, for example a surgical stapler and/or an energy device, and at least one endoscopic camera through the incisions into the patient. The surgical procedures are then performed by using the introduced tools, with the visualization aid provided by the camera. Generally, MIS provides multiple benefits, such as reduced patient scarring, less patient pain, shorter patient recovery periods, and lower medical treatment costs associated with patient recovery. In some embodiments, MIS may be performed withing a surgical or operating arena using robotic systems that include one or more robotic arms for manipulating surgical instruments based on commands from an operator.

SUMMARY

Aspects of the disclosure include a mounting kit or assembly that can be used to convert a cable hole on a support structure to a mounting interface for an auxiliary device. Representatively, the mounting kit or assembly may be used to convert a cable hole on a control tower or an auxiliary cart to a mounting interface for an auxiliary device such as a digital hub. For example, standard auxiliary video carts may provide visualization and/or documentation of procedures performed within the operating arena and therefore typically require that a digital hub be near the cart, for example, near the cart sidewall. Carts, however, typically have sidewalls made of sheet metal and it is not practical to drill additional holes for mounting additional devices. Thus, there is no standard way of attaching devices that must be near the sidewall of the cart, such as a digital hub, to the cart. In addition, since the cart may be mobile, mounting the digital hub to another structure near the cart, for example, a nearby wall or table is also not a practical solution for ensuring close proximity between the cart and hub. When the cart is moved to another location within the operating arena, the digital hub may then also need to be moved and mounted to another surface closer to the cart. The mounting kit or assembly disclosed herein therefore solves these challenges without having to drill new holes into the cart or otherwise modify the existing cart structure.

Representatively, in one aspect the disclosure is directed to a bracket assembly for a surgical robotic system. The bracket assembly may include a bracket having a first side defining a mounting interface and a second side defining an out of plane portion dimensioned for insertion within a cable opening of an auxiliary video cart; and a bracket securing member having an engaging member dimensioned to slidably engage the out of plane portion and a plate dimensioned to support the engaging member and secure the bracket to the auxiliary video cart. In one aspect, the first side and the second side extend from a distal end to a proximal end of a rectangular base portion of the bracket, the out of plane portion is near the distal end and the mounting interface is near the proximal end. In another aspect, the mounting interface may include a recessed region and a pair of slots along opposing sides of the recessed region that are operable to receive a mounting portion of a VESA® quick release adapter coupled to a digital hub. In another aspect, the pair of slots are formed by a pair of tabs that overlap the recessed region and are dimensioned to retain the mounting portion to secure the auxiliary device to the auxiliary video cart. In some aspects the out of plane portion comprises an elongated shape that is complimentary to a shape of the cable opening of the auxiliary video cart. In still further aspects, the out of plane portion includes a sidewall extending from the second side and a slot formed through the sidewall. In some aspects, the plate includes a planar portion partially surrounded by a rim and the engaging member comprises a tab extending from the rim and dimensioned for insertion within the slot. In some aspects, the tab is spaced a distance from the planar portion and operable to slide into the slot in a direction parallel to a plane of the second side. In still further aspects, each of the out of plane portion and the plate include at least one screw hole that align with one another and are operable to receive at least one wing nut for securing the bracket and the bracket securing member to the auxiliary video cart.

In another aspect, a bracket assembly kit for a surgical robotic system is disclosed. The bracket assembly kit includes a bracket having a first side defining a mounting interface for a mounting bracket coupled to an auxiliary device and a second side having an out of plane portion formed by a sidewall including a slot formed therein; a bracket securing member having an engaging member dimensioned to slidably engage the slot formed by the sidewall of the out of plane portion; and a pair of fasteners operable for insertion through the bracket and the bracket securing member to secure the bracket and the bracket securing member to an existing cable opening of a support structure. In some aspects, the bracket includes a rectangular shape having a distal end and a proximal end, and the out of plane portion is closer to the distal end than the engaging member. In some aspects, the mounting interface includes a first tab and a second tab that are arranged along opposing sides of a recessed region, and the first tab and the second tab are dimensioned to receive a plate portion of a VESA® quick release adapter coupled to the auxiliary device. In some aspects, the sidewall of the out of plane portion extends to a planar top surface having a length dimension greater than a width dimension. In still further aspects, the planar top surface includes a racetrack shape dimensioned for insertion within the existing cable opening of the support structure. In some aspects, the slot extends through the sidewall in a direction parallel to a plane of the second side. In still further aspects, the plate includes a planar portion partially surrounded by a rim that matches a perimeter of the out of plane portion and provides a receiving space for the out of plane portion. In some aspects, the engaging member includes a tab extending from the rim. In some aspects, the tab includes a thickness that is less than a thickness of the rim and is spaced a distance from the planar portion such that the tab is operable to slide into the slot formed in the out of plane portion. In some aspects, the pair of fasteners include at least one wing nut operable for insertion through a screw hole in the bracket and bracket securing member. In some aspects, the support structure is an auxiliary video cart and the auxiliary device includes a digital hub.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

DETAILED DESCRIPTION

Figure 1:
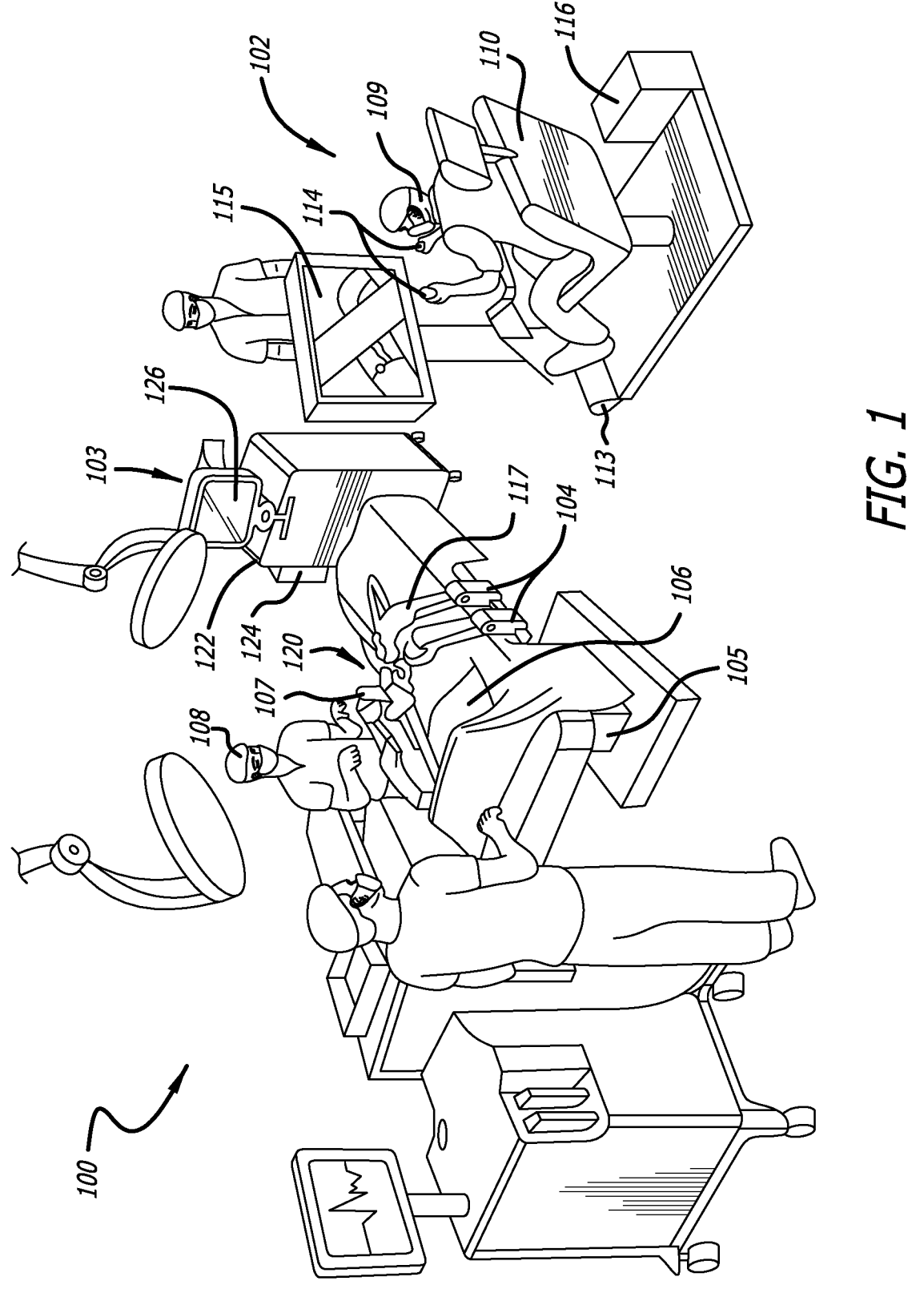
FIG. 1 is an overview schematic of an operating room arrangement with a surgical robotic system.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

In addition, the terminology used herein is for the purpose of describing particular aspects only and is not intended to be limiting of the invention. Spatially relative terms, such as "beneath", "below", "lower", "above", "upper", and the like may be used herein for ease of description to describe one element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (e.g., rotated 90 degrees or at other orientations) and the spatially relative descriptors used herein interpreted accordingly.

As used herein, the singular forms "a", "an", and "the" are intended to include the plural forms as well, unless the context indicates otherwise. It will be further understood that the terms "comprises" and/or "comprising" specify the presence of stated features, steps, operations, elements, and/or components, but do not preclude the presence or addition of one or more other features, steps, operations, elements, components, and/or groups thereof.

The terms "or" and "and/or" as used herein are to be interpreted as inclusive or meaning any one or any combination. Therefore, "A, B or C" or "A, B and/or C" mean "any of the following: A; B; C; A and B; A and C; B and C; A, B and C." An exception to this definition will occur only when a combination of elements, functions, steps or acts are in some way inherently mutually exclusive.

Moreover, the use of relative terms throughout the description may denote a relative position or direction. For example, "distal" may indicate a first direction away from a reference point, e.g., away from a user. Similarly, "proximal" may indicate a location in a second direction opposite to the first direction, e.g., toward the user. Such terms are provided to establish relative frames of reference, however, and are not intended to limit the use or orientation of any particular surgical robotic component to a specific configuration described in the various embodiments below.

Referring to FIG. 1, this is a pictorial view of an example surgical robotic system 100 in an operating arena. It should be appreciated, however, that the operating room scene in FIG. 1 is illustrative and may not accurately represent certain medical practices. The surgical robotic system 100 includes a user console 102, a control tower 103, and one or more surgical robots 120, including robotic arms 104 at a surgical robotic platform 105, e.g., an operating table, a bed, etc. The system 100 can incorporate any number of devices, tools, or accessories used to perform surgery on a patient 106. For example, the system 100 may include one or more surgical tools 107 used to perform surgery. A surgical tool 107 may be an end effector that is attached to a distal end of a surgical arm 104, for executing a surgical procedure. In some aspects, surgical tool 107 may include one or more of an energy tool, a harmonic tool, a stapler, or any other surgical tool or device.

Each surgical tool 107 may be manipulated manually, robotically, or both, during the surgery. For example, the surgical tool 107 may be a tool used to enter, view, or manipulate an internal anatomy of the patient 106. In an embodiment, the surgical tool 107 may be a grasper that can grasp tissue of the patient and/or an energy tool that can emit energy to cut, coagulate, desiccate and/or fulgurate the grasped tissue. The surgical tool 107 may be controlled manually, by a bedside operator 108; or it may be controlled robotically, via actuated movement of the surgical robotic arm 104 to which it is attached. The robotic arms 104 are shown as a table-mounted system, but in other configurations the arms 104 may be mounted in a cart, ceiling or sidewall, or in another suitable structural support.

Generally, a remote operator 109, such as a surgeon or other operator, may use the user console 102 to remotely manipulate the arms 104 and/or the attached surgical tools 107, e.g., teleoperation. Teleoperation may be engaged or disengaged based on the user actions. It should be understood that "engaging" the teleoperation mode is intended to refer to an operation in which, for example, a UID or foot pedal that is prevented from controlling the surgical instrument, is transitioned to a mode (e.g., a teleoperation mode) in which it can now control the surgical instrument. On the other hand, disengaging the teleoperation mode is intended to refer to an operation which occurs when the system is in a teleoperation mode, and then transitioned to a mode (non-teleoperation mode) in which the UID or foot pedal can no longer control the surgical instrument.

The user console 102 may be located in the same operating arena or room as the rest of the system 100, as shown in FIG. 1. In other environments however, the user console 102 may be located in an adjacent or nearby room, or it may be at a remote location, e.g., in a different building, city, or country. The user console 102 may comprise a seat 110, one or more user interface devices, for example, foot-operated controls 113 or handheld user input devices (UID) 114, and at least one user display 115 that is configured to display, for example, a view of the surgical site inside the patient 106. In the example user console 102, the remote operator 109 is sitting in the seat 110 and viewing the user display 115 while manipulating a foot-operated control 113 and a handheld UID 114 in order to remotely control the arms 104 and the surgical tools 107 (that are mounted on the distal ends of the arms 104).

In some variations, the bedside operator 108 may also operate the system 100 in an "over the bed" mode, in which the bedside operator 108 (user) is now at a side of the patient 106 and is simultaneously manipulating a robotically-driven tool (end effector as attached to the arm 104), e.g., with a handheld UID 114 held in one hand, and a manual laparoscopic tool. For example, the bedside operator's left hand may be manipulating the handheld UID to control a robotic component, while the bedside operator's right hand may be manipulating a manual laparoscopic tool. Thus, in these variations, the bedside operator 108 may perform both robotic-assisted minimally invasive surgery and manual laparoscopic surgery on the patient 106.

During an example procedure (surgery), the patient 106 is prepped and draped in a sterile fashion to achieve anesthesia. Initial access to the surgical site may be performed manually while the arms of the robotic system 100 are in a stowed configuration or withdrawn configuration (to facilitate access to the surgical site). To create a port for enabling introduction of a surgical instrument into the patient 106, a trocar assembly may be at least partially inserted into the patient through an incision or entry point in the patient (e.g., in the abdominal wall). The trocar assembly may include a cannula or trocar, an obturator, and/or a seal. In some variations, the trocar assembly can include an obturator such as a needle with a sharpened tip for penetrating through a patient's skin. The obturator may be disposed within the lumen of the cannula when being inserted into the patient 106, and then removed from the cannula such that a surgical instrument may be inserted through the lumen of the cannula. Once positioned within the body of the patient 106, the cannula may provide a channel for accessing a body cavity or other site within the patient 106, for example, such that one or more surgical instruments or tools (e.g., an energy tool) can be inserted into a body cavity of the patient 106, as described further herein. It will be understood that the cannula as described herein may be part of a trocar, and can optionally include an obturator or other components.

Once access is completed, initial positioning or preparation of the robotic system 100 including its arms 104 may be performed. Next, the surgery proceeds with the remote operator 109 at the user console 102 utilizing the foot-operated controls 113 and the UIDs 114 to manipulate the various end effectors and perhaps an imaging system, to perform the surgery. Manual assistance may also be provided at the procedure bed or table, by sterile-gowned bedside personnel, e.g., the bedside operator 108 who may perform tasks such as retracting tissues, performing manual repositioning, and tool exchange upon one or more of the robotic arms 104. Non-sterile personnel may also be present to assist the remote operator 109 at the user console 102. When the procedure or surgery is completed, the system 100 and the user console 102 may be configured or set in a state to facilitate post-operative procedures such as cleaning or sterilization and healthcare record entry or printout via the user console 102.

In one embodiment, the remote operator 109 holds and moves the UID 114 to provide an input command to move a robot arm actuator 117 in the robotic system 100. The UID 114 may be communicatively coupled to the rest of the robotic system 100, e.g., via a console computer system 116. Representatively, in some embodiments, UID 114 may be a portable handheld user input device or controller that is ungrounded with respect to another component of the surgical robotic system. For example, UID 114 may be ungrounded while either tethered or untethered from the user console. The term "ungrounded" is intended to refer to implementations where, for example, both UIDs are neither mechanically nor kinematically constrained with respect to the user console. For example, a user may hold a UID 114 in a hand and move freely to any possible position and orientation within space only limited by, for example, a tracking mechanism of the user console. The UID 114 can generate spatial state signals corresponding to movement of the UID 114, e.g., position and orientation of the handheld housing of the UID, and the spatial state signals may be input signals to control a motion of the robot arm actuator 117. The robotic system 100 may use control signals derived from the spatial state signals, to control proportional motion of the actuator 117. In one embodiment, a console processor of the console computer system 116 receives the spatial state signals and generates the corresponding control signals. Based on these control signals, which control how the actuator 117 is energized to move a segment or link of the arm 104, the movement of a corresponding surgical tool that is attached to the arm may mimic the movement of the UID 114. Similarly, interaction between the remote operator 109 and the UID 114 can generate for example a grip control signal that causes a jaw of a grasper of the surgical tool 107 to close and grip the tissue of patient 106.

The surgical robotic system 100 may include several UIDs 114, where respective control signals are generated for each UID that control the actuators and the surgical tool (end effector) of a respective arm 104. For example, the remote operator 109 may move a first UID 114 to control the motion of an actuator 117 that is in a left robotic arm, where the actuator responds by moving linkages, gears, etc., in that arm 104. Similarly, movement of a second UID 114 by the remote operator 109 controls the motion of another actuator 117, which in turn moves other linkages, gears, etc., of the robotic system 100. The robotic system 100 may include a right arm 104 that is secured to the bed or table to the right side of the patient, and a left arm that is at the left side of the patient. An actuator 117 may include one or more motors that are controlled so that they drive the rotation of a joint of the arm(s) 104, to for example change, relative to the patient, an orientation of an endoscope or a grasper of the surgical tool 107 that is attached to that arm. Motion of several actuators 117 in the same arm 104 can be controlled by the spatial state signals generated from a particular UID 114. The UIDs 114 can also control motion of respective surgical tool graspers. For example, each UID 114 can generate a respective grip signal to control motion of an actuator, e.g., a linear actuator, that opens or closes jaws of the grasper at a distal end of surgical tool 107 to grip tissue within patient 106. In some aspects, the surgical tool grasper may be a surgical stapler or energy tool and the UIDs 114 are used to control the opening or closing of the jaw of the surgical stapler or energy tool as well as the release of staples and/or energy application through the tissue. When the user is finished controlling the surgical tools with the UIDs 114, the user may dock (i.e., store) the UIDs 114 with docking stations or UID holders located on the console 102.

In some aspects, the communication between the platform 105 and the user console 102 may be through a control tower 103 to translate user commands that are received from the user console 102 (and more particularly from the console computer system 116) into robotic control commands that are transmitted to the arms 104 on the robotic platform 105. The control tower 103 may also transmit status and feedback from the platform 105 back to the user console 102. The communication connections between the robotic platform 105, the user console 102, and the control tower 103 may be via wired and/or wireless links, using any suitable ones of a variety of data communication protocols. Any wired connections may be optionally built into the floor and/or walls or ceiling of the operating room. The robotic system 100 may provide video output to one or more displays 126, including displays within the operating room as well as remote displays that are accessible via the Internet or other networks. The video output or feed may also be encrypted to ensure privacy and all or portions of the video output may be saved to a server or electronic healthcare record system. In some aspects, the one or more displays 126 may be mounted to an auxiliary video cart 122 of control tower 103. In addition, a digital hub 124 may be provided to manage connections and/or data transfer between the robotic platform 105, the user console 102, the display 126 and/or the control tower 103. As previously discussed, for optimal connectivity, digital hub 124 should be as close as possible to control tower 103. Thus, in some aspects, digital hub 124 is mounted to a sidewall of the control tower auxiliary cart 122 as shown. Representatively, digital hub 124 may be mounted to the sidewall of cart 122 by converting an existing hole (e.g., a cable hole) in the sidewall of cart 122 to a mounting interface for digital hub 124. For example, the sidewall(s) of cart 122 may include cable holes used to run electrical cables between devices within cart 122 and devices on or around cart 122. Typically, not all of the cable holes are used so at least one or more will remain open. The one or more cable holes that are open can therefore be converted to a mounting interface for hub 124 using the mounting or bracket assembly disclosed herein.

Figures 2, 3:
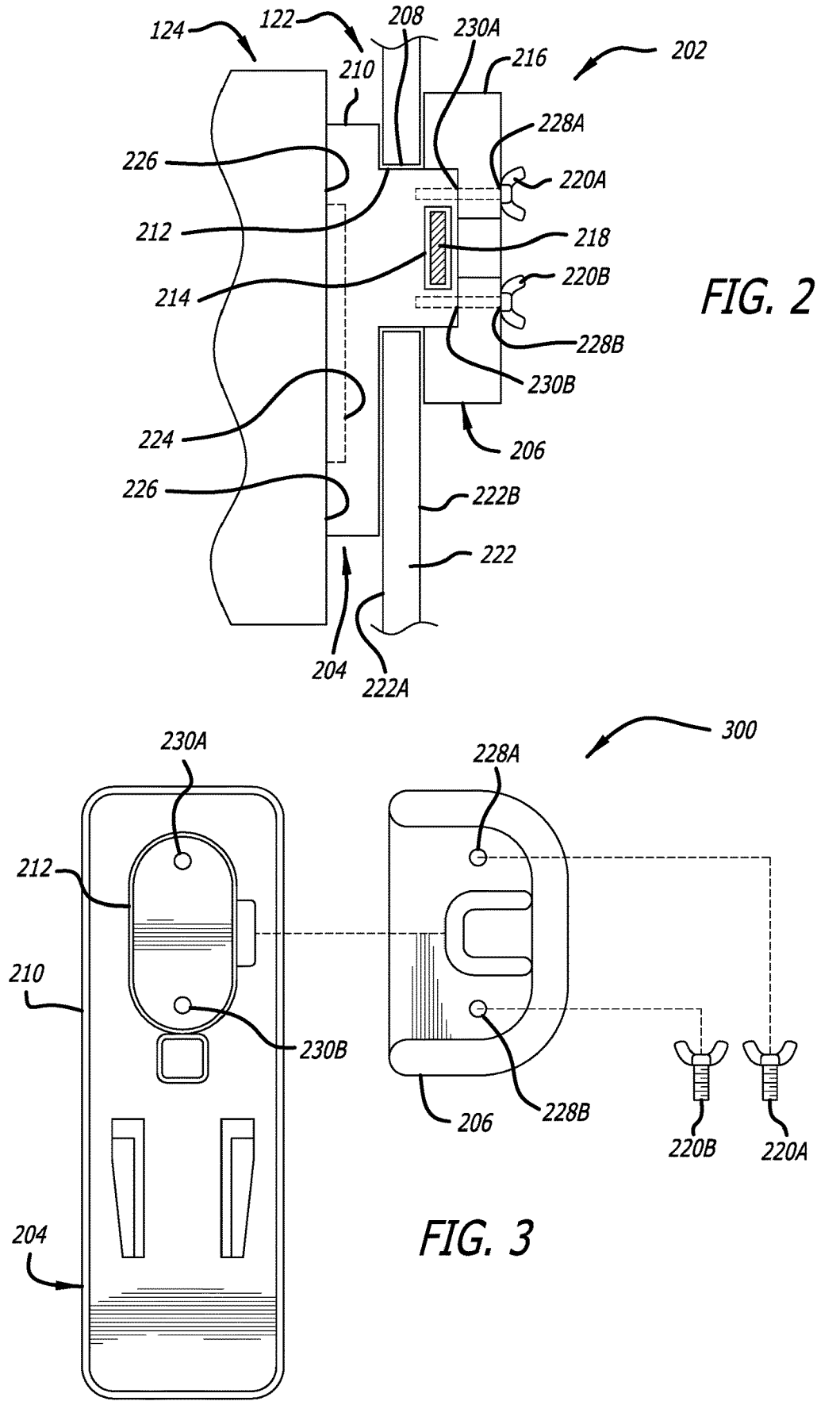
FIG. 2 is a cross-sectional side view of one aspect of a mounting assembly or kit for a surgical robotic system.
FIG. 3 is a top plan view of the mounting assembly or kit for the surgical robotic system of FIG. 2.

FIG. 2 illustrates a cross-sectional side view of one representative mounting or bracket assembly that can be used to convert an opening in the cart to a mounting interface for the digital hub. Representatively, FIG. 2 illustrates a sidewall 222 of cart 122 with digital hub 124 mounted thereto by mounting or bracket assembly 202. In one aspect, mounting or bracket assembly 202 may include an outer bracket 204 and an inner bracket securing member 206. Outer bracket 204 may include a substantially planar base portion 210 and an out of plane portion 212 that extends out of plane relative to base portion 210. The base portion 210 may be positioned along the outer side 222A of sidewall 222 and serve as the interface for mounting digital hub 124 to cart 122. Representatively, base portion 210 may have a mounting interface 226 along a side of base portion 210 that faces digital hub 124. Mounting interface 226 may be configured to receive mounting bracket 224 coupled to digital hub 124. In one aspect, the mounting bracket 224 may be, for example, a mounting plate portion of a VESA® quick release adapter, also referred to as stock keeping unit (SKU) STAND-VAD2. In this aspect, mounting interface 226 may be configured to receive the mounting plate portion of the VESA® quick release adapter as will be described in more detail in reference to FIGS. 7 and 10.

Referring now to out of plane portion 212, out of plane portion 212 may be configured to extend through opening 208 in sidewall 222 and extend beyond the inner side 222B of sidewall 222. The opening 208 may be a cable opening in sidewall 222 sized to accommodate the passage of one or more cables from one or more electronic devices within cart 122 outside of the cart 122. Out of plane portion 212 may have a size and shape complimentary to that of opening 208 but slightly smaller such that it fits through opening 208. Out of plane portion 212 may further include a slot 214 formed in the portion of out of plane portion 212 extending beyond inner side 222B. Slot 214 may run parallel to the plane of the substantially planar base portion 210. In this aspect, the opening to slot 214 may be through a sidewall of the out of plane portion 212 as will be discussed in more detail in reference to FIGS. 4-6. Slot 214 is configured to receive a portion of inner bracket securing member 206 to help hold outer bracket 204 (with digital hub 124 attached thereto) along sidewall 222 without any other user assistance. In other words, when the portion of inner bracket securing member 206 is positioned through slot 214, outer bracket 204 (and digital hub 124) remains along sidewall 222 without the user having to hold or support any portion of the bracket assembly 202. In this aspect, once the outer and inner bracket portions 204 and 206 are connected together, the remainder of the assembly process can be done with one hand.

Referring now to inner bracket securing member 206, inner bracket securing member 206 may be positioned along the inner side 222B of sidewall 222 and is configured to secure the outer bracket 204 to sidewall 222. In this aspect, inner bracket securing member 206 includes a base or plate portion 216 and an engaging member 218. The base or plate portion 216 is configured to be positioned on and contact the inner side 222B of sidewall 222 and protruding portion 212. The engaging member 218 extends in a direction parallel to the base or plate portion 216 such that it may be inserted into slot 214 (e.g., running in the same direction). For example, engaging member 218 may be a protruding or tab like structure that extends from a raised portion of engaging member 218 and parallel to the base or plate portion 216. Engaging member 218 may have a free end that can be inserted into slot 214 to couple the outer bracket 204 to inner bracket securing member 206.

In still further aspects, mounting or bracket assembly 202 may include fasteners 220A and 220B. Fasteners 220A-B may be used to secure the inner bracket securing member 206 to the outer bracket 204, which in turn, secures the bracket assembly 202 and associated digital hub 124 to cart 122. Representatively, fasteners 220A-B may be wing nuts or screws that can be inserted through fastener openings 228A, 228B of inner bracket securing member 206 and fastener openings 230A, 230B of outer bracket 204. For example, fastener opening 228A may be a screw hole that extends entirely through inner bracket securing member 206. Fastener opening 228A may align with fastener opening 230A (e.g., a screw hole) through the out of plane portion 212 of outer bracket 204. Fastener 220A may then be inserted through opening 228A and into fastener opening 230A to couple the two bracket members together. Similarly, fastener opening 228B may extend entirely through inner bracket securing member 206 and align with fastener opening 230B through the out of plane portion 212 of outer bracket 204. Fastener 220B may then be inserted through opening 228B and into fastener opening 230B to further couple the two bracket members together. In the representative example where fasteners 220A-B are wing nuts, the wing nuts may be rotated once positioned in the fastener openings to further drive the fasteners 220A-B through the fastener openings 230A-B of outer bracket 204 and tighten or otherwise pull the bracket members 204, 206 closer together.

Thus, it should be recognized that in some aspects, the mounting or bracket assembly 202 may be considered a kit 300 comprised of outer bracket 204, inner bracket securing member 206 and fasteners 220A-B as shown in FIG. 3. Representatively, FIG. 3 illustrates a top plan view of a kit 300 including each of the outer bracket 204, inner bracket securing member 206 and fastener 220A-B described in reference to FIG. 2 prior to assembly. The kit may further be understood as composed of a universal mounting or bracket assembly that can be used to mount an auxiliary component or device to any support structure having an existing opening. For example, the kit can be used to convert a cable opening in an auxiliary cart to a mounting interface for a digital hub as disclosed herein. In other aspects, the cable opening may be in another type of support structure and used to mount another type of auxiliary member or device to the support structure using the existing cable opening. In this aspect, the kit provides a universal mounting interface that simplifies the mounting process and avoids the need to drill or otherwise make new openings in a support structure wall.

Figure 4:
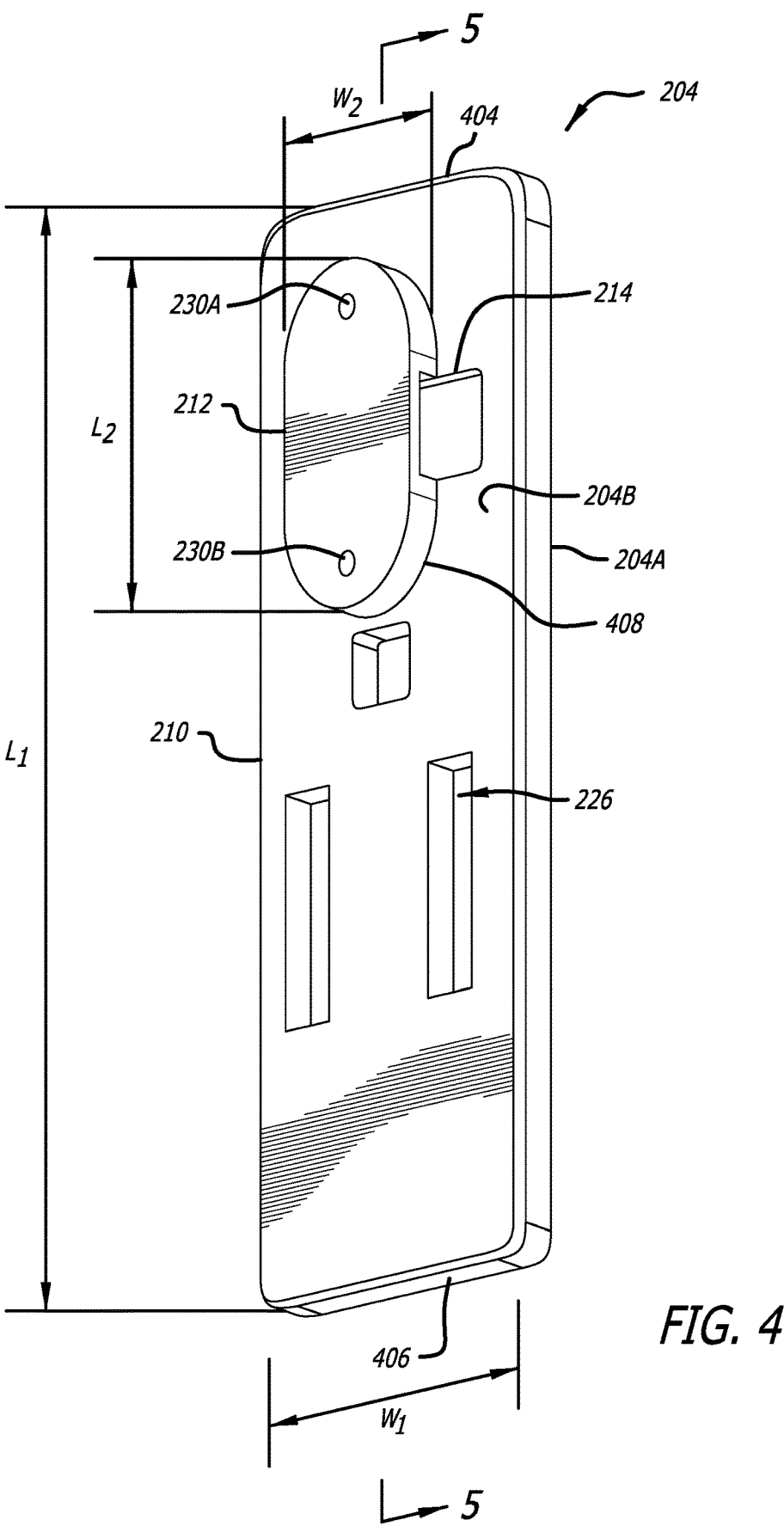
FIG. 4 is a side perspective view of another aspect of a mounting assembly or kit for a surgical robotic system.

Referring now to the outer bracket in more detail, FIG. 4 illustrates a back side perspective view of outer bracket assembly 204 previously discussed in reference to FIGS. 2-3. From this view, it can be seen that outer bracket assembly 204 includes base portion 210 having a front side 204A and a back side 204B that extend between a distal end 404 and proximal end 406 of base portion 210. In some aspects, base portion 210 may have an elongated shape such that its length (L1) is greater than its width (W1). For example, in some aspects, base portion 210 may have a rectangular shape as shown. Front side 204A may be configured to interface with the digital hub 124 and back side 204B may be configured to interface with cart 122. For example, front side 204A may form a mounting interface 226 for the digital hub 124 as will be described in more detail in reference to FIG. 6. Back side 204B may be substantially planar except that out of plane portion 212 may be understood as extending out of plane relative to the plane of back side 204B. Out of plane portion 212 may have an elongated shape such that its length (L2) is greater than its width (W2). For example, out of plane portion 212 may have an elongated oval or racetrack shape as shown. It should be understood, however, that out of plane portion 212 may have any shape and/or size suitable for insertion within an opening of the support structure. It can further be understood from this view that slot 214 is formed through the sidewall 408 of out of plane portion 212. In addition, fastener openings 230A and 230B may be formed through the top surface of out of plane portion 212 as shown.

Figure 5:
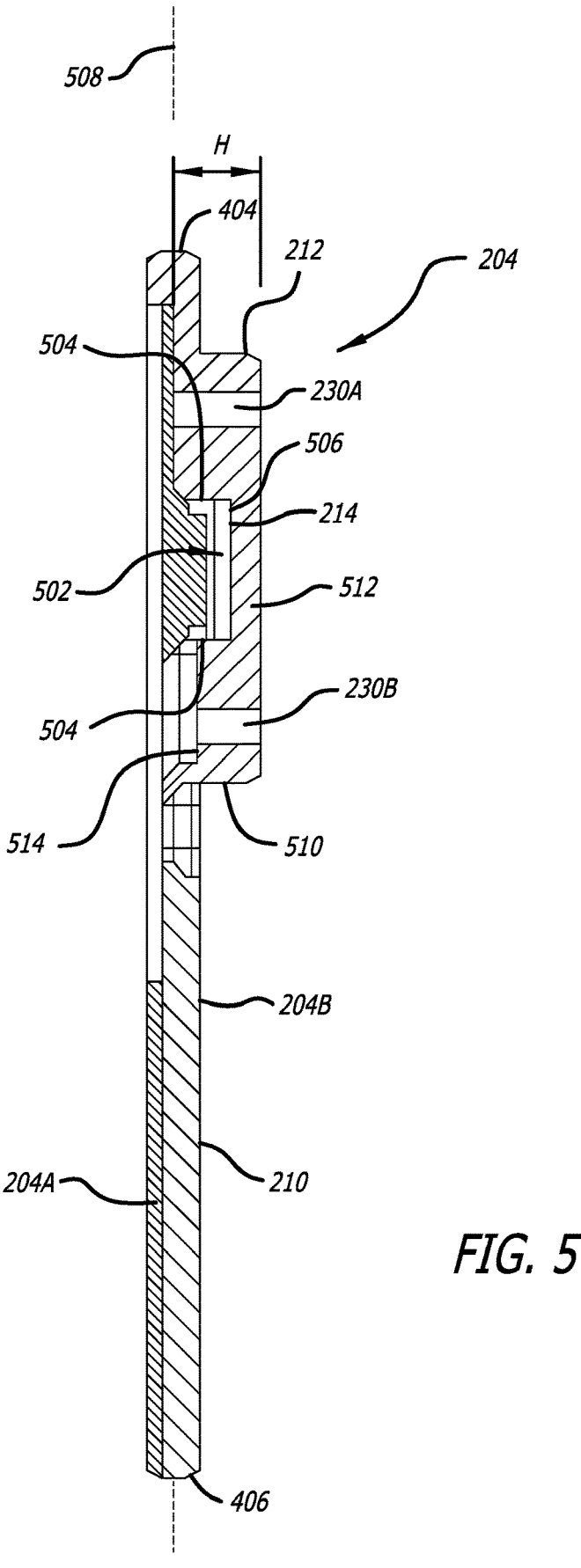
FIG. 5 is a side perspective view of another aspect of a mounting assembly or kit for a surgical robotic system.

These aspects can be further seen more clearly from FIG. 5, which illustrates a cross-sectional side perspective view through line 5-5 of FIG. 4. Representatively, as can be seen from FIG. 5, out of plane portion 212 includes a sidewall 510 that extends out of the plane 508 of base portion 210 to a substantially flat or planar top side or surface 512. In this aspect, out of plane portion 212 or sidewall 510 may be considered as having a height (H). Sidewall 510 may extend out of the plane 508 of base portion 210 by a distance that is greater than, for example, the thickness of sidewall 222. In this aspect, slot 214 will be positioned along a side of the cart sidewall opposite the base portion 210 when out of plane portion 212 is inserted through the sidewall opening, as previously discussed. As can further be seen from this view, slot 214 runs parallel to plane 508 and/or top surface 512 of out of plane portion 212. Representatively, slot 214 is formed by sidewalls 504 that extend to top side 506 and define a channel within out of plane portion 212 that runs parallel to plane 508 and/or top surface 512. An opening 502 to slot 214 is formed through sidewall 510 of out of plane portion 212. In this aspect, the previously discussed engaging member of the inner bracket securing member slides into the slot 214 through opening 502 in a direction parallel to plane 508.

It can further be seen from FIG. 5 that fastener openings 230A, 230B extend through out of plane portion 212. Representatively, fastener openings 230A, 230B extend from top surface 512 to a bottom side or surface 514 of out of plane portion 212 such that they run perpendicular to plane 508. Fastener openings 230A, 230B may be arranged distally and proximally to slot 214 as shown, or may have other arrangements. It is further contemplated that while two fastener openings 230A, 230B are described, any number of fastener openings suitable for securing the mounting assembly to the cart sidewall may be used.

Figure 6:
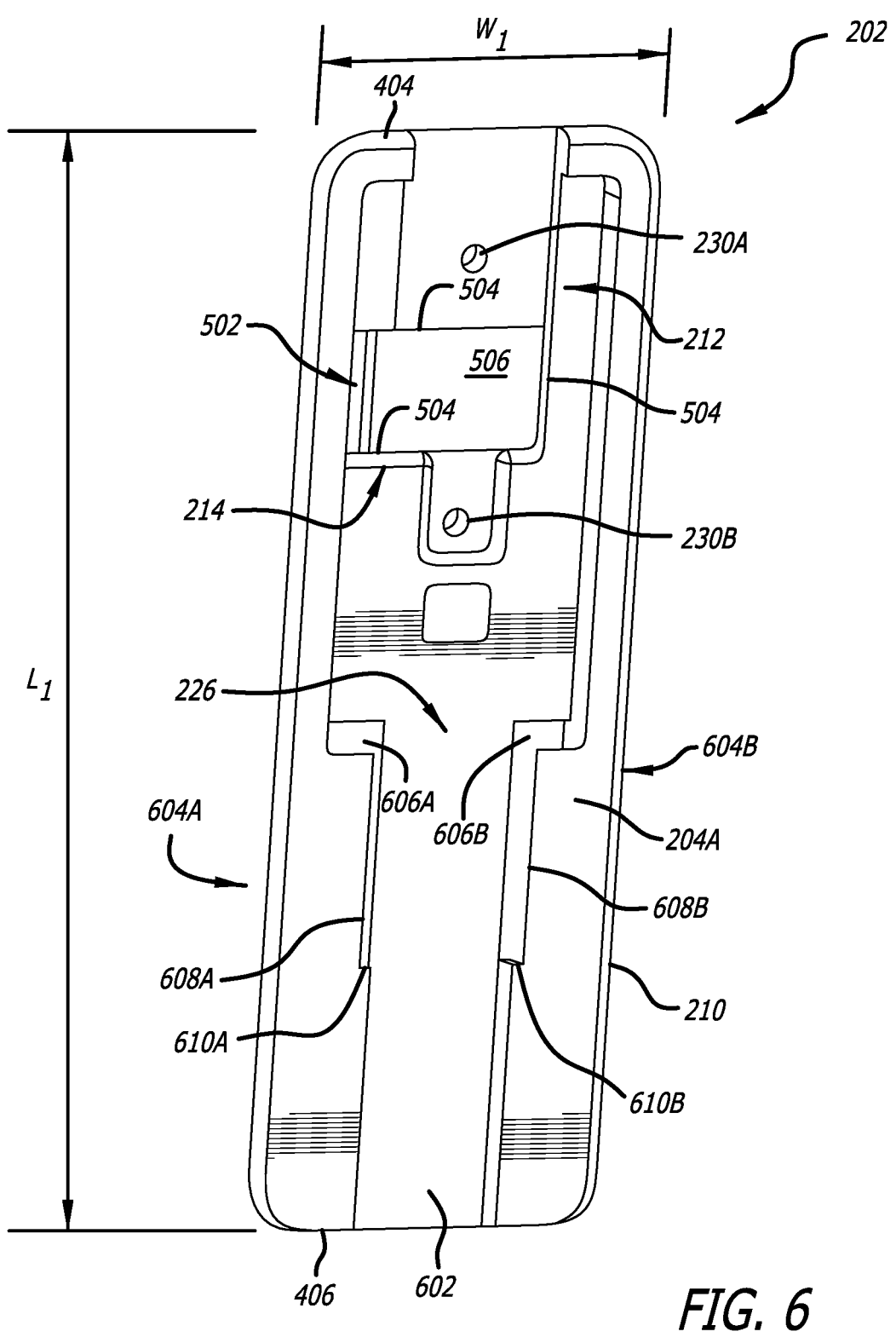
FIG. 6 is a top perspective view of another aspect of a mounting assembly or kit for a surgical robotic system.

FIG. 6 illustrates a front side perspective view of outer bracket assembly 204 previously discussed in reference to FIGS. 2-5. From this view, the orientation and arrangement of slot 214 within out of plane portion 212 of outer bracket assembly 204 can be more clearly seen. Representatively, slot 214 is shown as a channel formed by sidewalls 504 and top side 506 formed within the out of plane portion 212. Slot 214 runs in a widthwise direction (e.g., parallel to width (W1)) and is parallel to the plane 508 as previously discussed. Slot 214 may further be positioned closer to the distal end 404 than the proximal end 406 of bracket 202. The opening 502 to slot 214 is further shown formed through one of sidewalls 504, which also form the out of plane portion 212.

Mounting interface 226 may be formed near the proximal end 406 of bracket 202. As previously discussed, mounting interface 226 may be dimensioned to receive a mounting bracket attached to the auxiliary device. For example, mounting interface 226 may be dimensioned to receive a mounting plate portion of a VESA® quick release adapter. Representatively, in one aspect, mounting interface 226 may include an elongated recessed region 602 formed in the front side 204A of base portion 210. A pair of slots 604A and 604B are further formed along opposing sides of the recessed region 602. Slots 604A, 604B may include openings 606A, 606B formed within recessed region 602 and tabs 608A, 608B that overlap openings 606A, 606B. Tabs 608A, 608B may be formed by portions of front side 204A such that they are out of plane relative to openings 606A, 606B. In this aspect, a space or gap is formed between tabs 608A, 608B and recessed region 602 for receiving a portion of the mounting bracket. Representatively, a portion of a mounting bracket attached to the digital hub may be inserted within slots 604A, 604B in a direction parallel to the plane of recessed region 602. Tabs 608A, 608B may further include end stops 610A, 610B at one end. Once the portion of the mounting bracket is inserted within slots 604A, 604B, tabs 608A, 608B overlap the mounting bracket, and prevent mounting bracket from moving in a direction perpendicular to the plane of recessed region 602. End stops 610A, 610B contact the end of the bracket to prevent a further sliding movement in a direction parallel to the plane.

Figure 7:
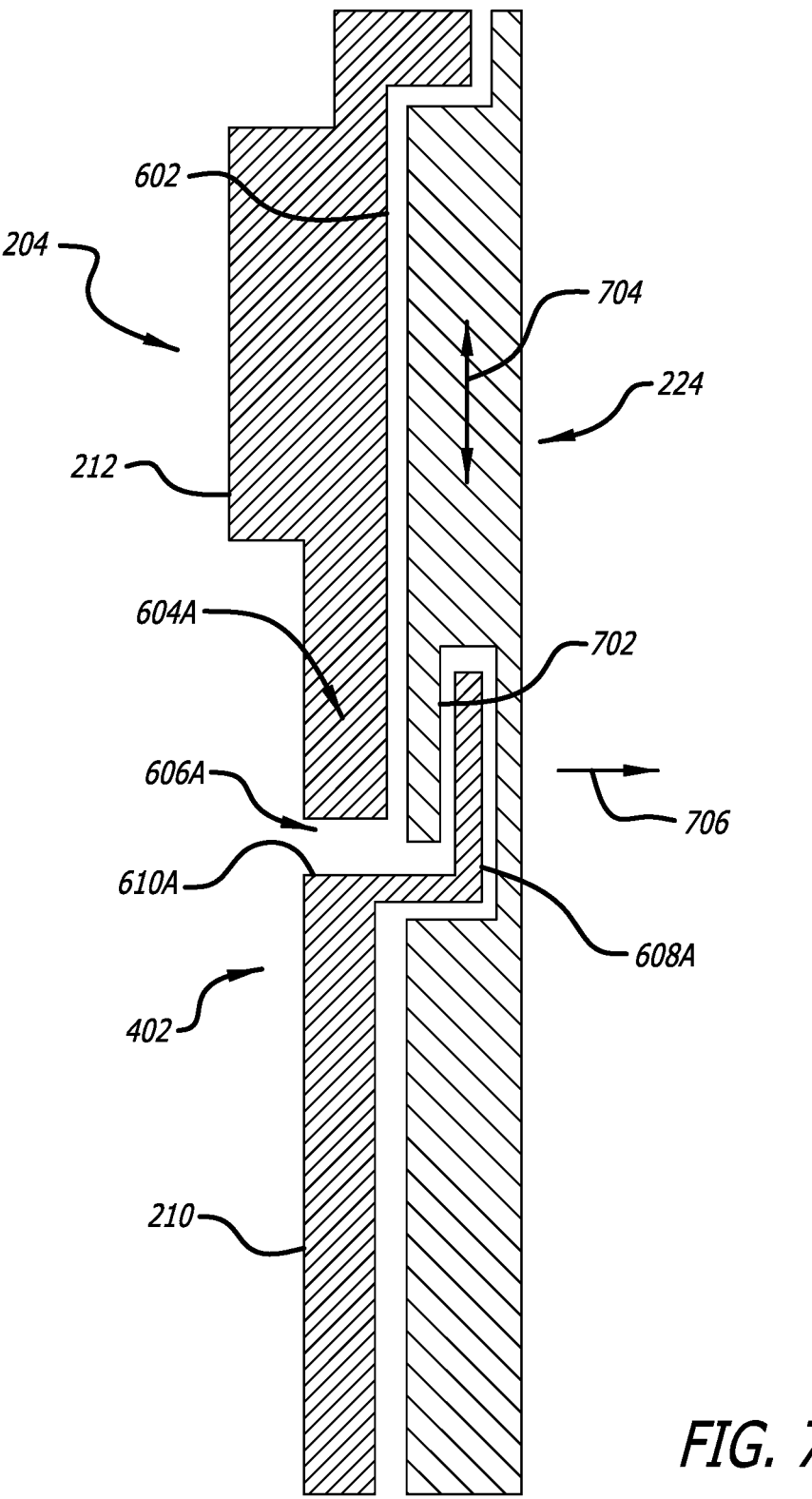
FIG. 7 is a cross-sectional side view of another aspect of a mounting assembly or kit for a surgical robotic system.

Representatively, FIG. 7 shows a cross-sectional side view of outer bracket 204 having a mounting interface 226 with the mounting bracket 224 inserted therein. From this view, it can be seen that mounting bracket 224 may include a protruding portion 702. Protruding portion 702 may have any size and shape suitable to be inserted into slot 604A, and interlock with tab 608A, as previously discussed. Representatively, protruding portion 702 may be inserted into slot 604A by sliding mounting bracket 224 into outer bracket 204 in a direction of arrow 704. Once protruding portion 702 is inserted into slot 604A, further movement in the direction of arrow 704 is prevented by end stop 610A. In addition, a movement in a direction perpendicular to arrow 704, as illustrated by arrow 706, is prevented by tab 608A of outer bracket 204. In this aspect, mounting bracket 224 along with the device to which it is attached (e.g., digital hub 124 of FIG. 2), is mounted to outer bracket 204 and the support structure (e.g., cart 122) as previously discussed.

Figure 8:
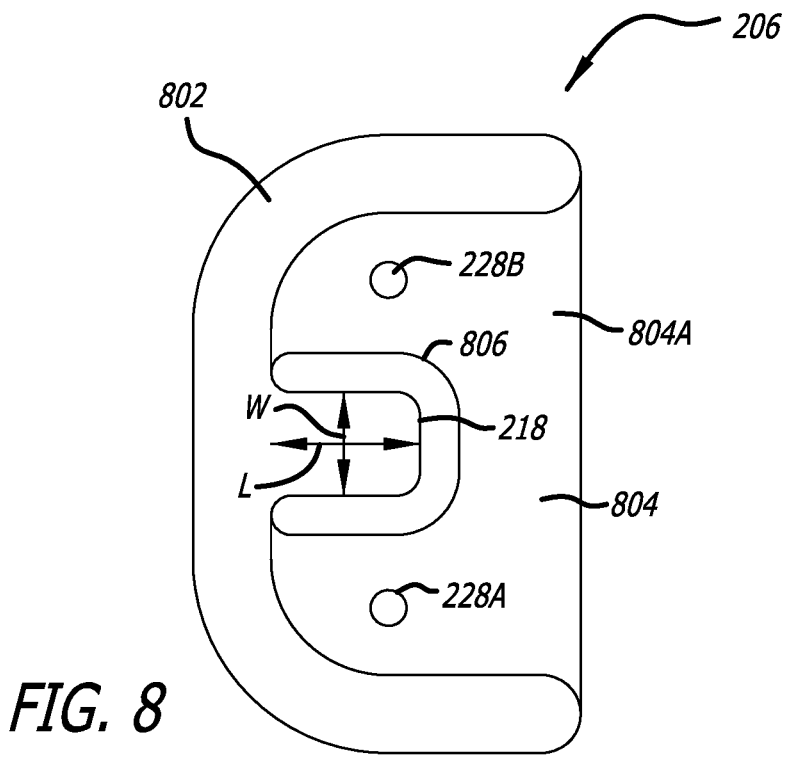
FIG. 8 is a top plan view of another aspect of a mounting assembly or kit for a surgical robotic system.
Figure 9:
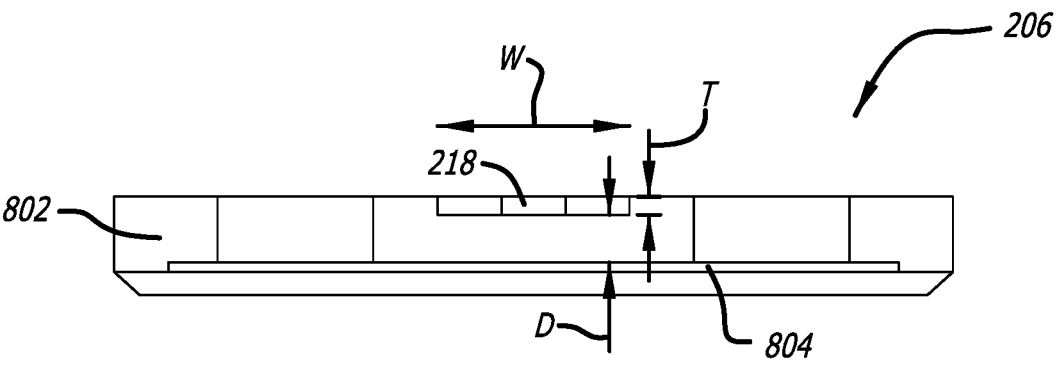
FIG. 9 is an end perspective view of another aspect of the mounting assembly or kit for a surgical robotic system of FIG. 8.

Referring now to FIG. 8, FIG. 8 is a top plan view illustrating aspects of the inner bracket securing member in more detail. From this view, it can be seen that inner bracket securing member 206 includes an engaging member 218 that extends from a raised portion 802 surrounding a plate portion 804. Representatively, plate portion 804 may be a substantially flat or planar structure that is larger than a size of the cable opening being converted to a mounting interface by the mounting or bracket assembly. Plate portion 804 may include a surface 804A. Surface 804A may be a surface intended to face the sidewall 222 of the cart 122 when mounting the mounting or bracket assembly to cart 122. The previously discussed openings 228A, 228B for securing bracket securing member 206 to outer bracket 204 are further shown formed through surface 804A. Raised portion 802 may be a rim or other similar structure that extends from a surface 804A of plate portion 804 and contacts the sidewall 222 of cart 122 when the mounting or bracket assembly is mounted to cart 122. Raised portion 802 spaces plate portion 804 a distance from sidewall 222 and defines a receiving space within inner bracket securing member 206 for the out of plane portion 212 of outer bracket 204. In this aspect, raised portion 802 may extend around surface 804A in a shape that conforms to the shape of the out of plane portion 212. For example, where out of plane portion 212 has an elongated or racetrack shape, raised portion 802 may have a similarly curved shape that matches the perimeter of the out of plane portion 212 so that the interfacing portions of out of plane portion 212 and raised portion 802 are complimentary to one another.

Engaging member 218 extends from a side of raised portion 802 and over opening 806 in plate portion 804. Engaging member 218 may be considered a tab or any other type of protruding member suitable for insertion within the slot 214 of outer bracket 204 as previously discussed. For example, engaging member 218 may be an elongated structure that extends in a direction parallel to, or is considered arranged parallel to, a plane of plate portion 804. Representatively, engaging member 218 may have a length (L) greater than its width (W). The length (L) and width (W) may be less than that of opening 806 and the surrounding plate portion 804. In addition, engaging member 218 may have a thickness that is less than that of the raised portion 802 such that engaging member 218 is spaced a distance from surface 804A of plate portion 804.

Representatively, as can be seen from the perspective end view of bracket securing member 206 illustrated in FIG. 8, engaging member 218 has a thickness (T), which is less than that of the raised portion 802. As a result, engaging member 218 is spaced a distance (D) from plate portion 804. This spacing or gap between engaging member 218 and plate portion 804 allows engaging member 218 to slide into slot 214 of outer bracket 204. This further creates a receiving area within securing member 206 for out of plane portion 212 to rest within and secure outer bracket 204 to the sidewall 222 of cart 122.

Figure 10A:
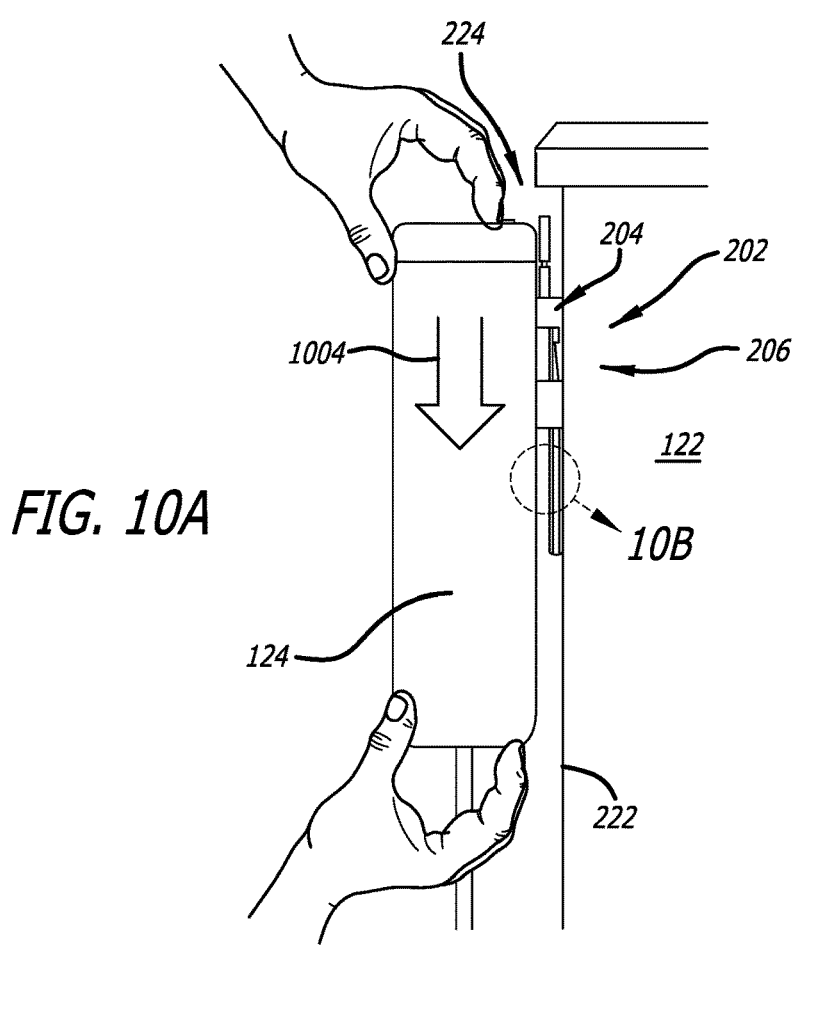
FIG. 10A is a side schematic view of another aspect of the mounting assembly or kit for a surgical robotic system during an assembly operation.
Figure 10B:
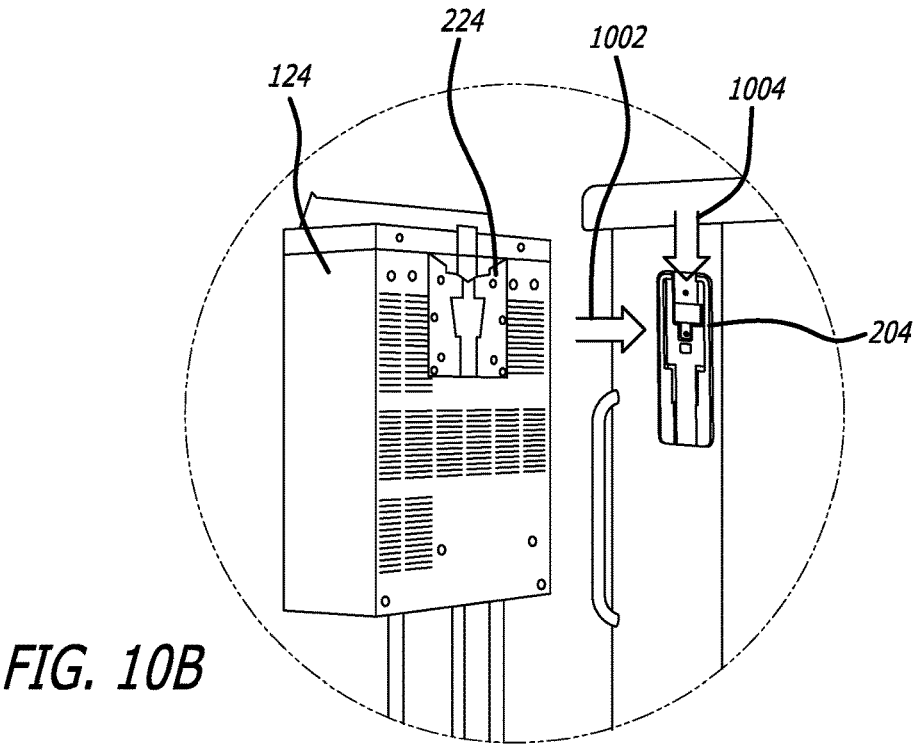
FIG. 10B is a magnified side schematic view of one aspect of the assembly operation of FIG. 10A.

A representative installation process for converting a cable hole of an auxiliary video cart to a mounting interface using the mounting or bracket assembly disclosed herein will now be described in reference to FIGS. 10A-10B. Representatively, FIG. 10A illustrates a side perspective view of cart 122 with the cable hole converted to a mounting interface using the mounting or bracket assembly 202. Representatively, outer bracket 204 of the mounting or bracket assembly 202 is mounted to the cable hole using bracket securing member 206 as previously discussed. In addition, as can be seen from the magnified view of FIG. 10B, which illustrates portion 10B of the assembly, mounting bracket 224 is attached to the digital hub 124. To then mount digital hub 124 to the converted opening in cart 122, digital hub 124 with the attached mounting bracket 224 is first moved toward bracket assembly 202 in cart 122 as illustrated by the arrow 1002. This aligns the mounting portion (e.g., protruding portion 702) of bracket 224 with the receiving portion (e.g., recessed region 602) of bracket assembly 202. Once aligned, the user may then slide hub 124 in a downward direction as illustrated by arrow 1004 to lock or otherwise mount the bracket 224 to bracket 202 and secure digital hub 124 to cart 122. It should further be understood that reversing these operations will unlock or otherwise release digital hub 124 from cart 122.

Figure 11:
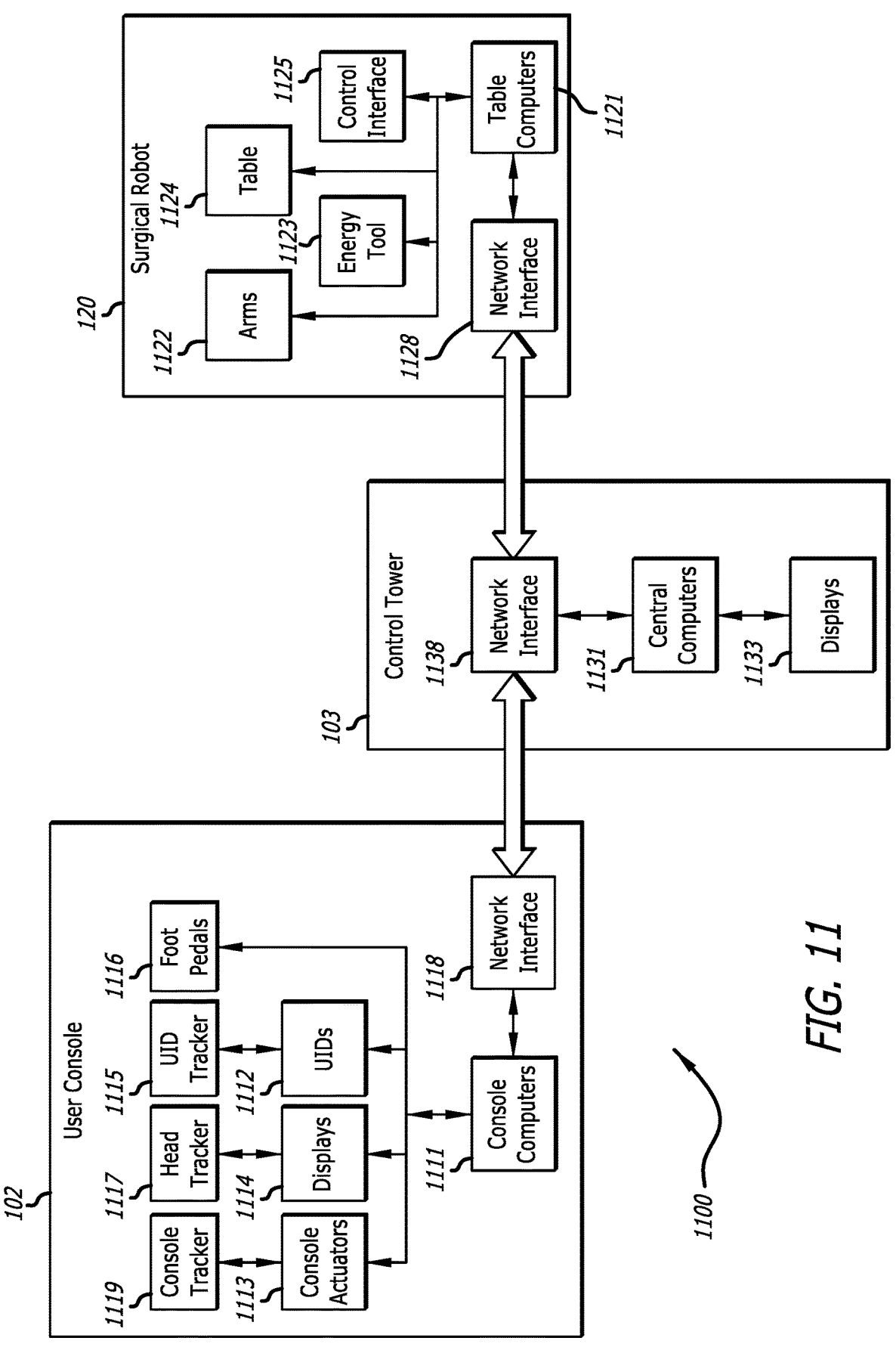
FIG. 11 is a block diagram of a computer portion of a surgical robotic system including an energy tool, in accordance with an aspect of the disclosure.

FIG. 11 is a block diagram of a computer portion of a surgical robotic system, which is operable to implement any one or more of the previously discussed operations. The exemplary surgical robotic system 1100 may include a user console 102, a surgical robot 120, and a control tower 103. The surgical robotic system 1100 may include other or additional hardware components; thus, the diagram is provided by way of example and not a limitation to the system architecture.

As described above, the user console 102 may include console computers 1111, one or more UIDs 1112, console actuators 1113, displays 1114, foot pedals 1116 and a network interface 1118. In addition, user console 102 may include a number of components, for example, a UID tracker(s) 1115, a display tracker(s) 1117 and a console tracker(s) 1119, for detecting various surgical conditions required for operation of the system (e.g., UID orientation, orientation of the surgeon relative to the display, orientation the console seat, etc.). It should further be understood that a user or surgeon sitting at the user console 102 can adjust ergonomic settings of the user console 102 manually, or the settings can be automatically adjusted according to user profile or preference. The manual and automatic adjustments may be achieved through driving the console actuators 1113 based on user input or stored configurations by the console computers 1111. The user may perform robot-assisted surgeries by controlling the surgical robot 120 using one or more master UIDs 1112 and foot pedals 1116. Positions and orientations of the UIDs 1112 are continuously tracked by the UID tracker 1115, and status changes are recorded by the console computers 1111 as user input and dispatched to the control tower 103 via the network interface 1118. Real-time surgical video of patient anatomy, instrumentation, and relevant software apps can be presented to the user on the high-resolution 3D displays 1114 including open or immersive displays.

The user console 102 may be communicatively coupled to the control tower 103. The user console also provides additional features for improved ergonomics. For example, the user console may be an open architecture system including an open display, although an immersive display, in some cases, may be provided. Furthermore, a highly adjustable seat for surgeons and master UIDs tracked through electromagnetic or optical trackers are included at the user console 102 for improved ergonomics.

The control tower 103 can be a mobile point-of-care cart housing touchscreen displays, computers that control the surgeon's robotically assisted manipulation of instruments, safety systems, graphical user interface (GUI), light source, and video and graphics computers. As shown in FIG. 11, the control tower 103 may include central computers 1131 including at least a visualization computer, a control computer, and an auxiliary computer, various displays 1133 including a team display and a nurse display, and a network interface 1138 coupling the control tower 103 to both the user console 102 and the surgical robot 120. The control tower 103 may offer additional features for user convenience, such as the nurse display touchscreen, soft power and E-hold buttons, user-facing USB for video and still images, and electronic caster control interface. The auxiliary computer may also run a real-time Linux, providing logging/ monitoring and interacting with cloud-based web services.

The surgical robot 120 may include an operating table 1124 with a plurality of integrated robotic arms 1122 that can be positioned over the target patient anatomy. An energy tool 1123 can be attached to or detached from the distal ends of the arms 1822, enabling the surgeon to perform various surgical procedures. The surgical robot 120 may also comprise control interface 1125 for manual or automated control of the arms 1122, table 1124, and tools 1123. The control interface can include items such as, but not limited to, remote controls, buttons, panels, and touchscreens. Other accessories such as trocars (sleeves, seal cartridge, and obturators) and drapes may also be needed to perform procedures with the system. In some variations, the plurality of the arms 1122 includes four arms mounted on both sides of the operating table 1124, with two arms on each side. For certain surgical procedures, an arm mounted on one side of the table can be positioned on the other side of the table by stretching out and crossing over under the table and arms mounted on the other side, resulting in a total of three arms positioned on the same side of the table 1124. The surgical tool can also comprise table computers 1121 and a network interface 1128, which can place the surgical robot 120 in communication with the control tower 103.

The foregoing description, for purposes of explanation, used specific nomenclature to provide a thorough understanding of the invention. However, it will be apparent to one skilled in the art that specific details are not required in order to practice the invention. Thus, the foregoing descriptions of specific aspects of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, and they thereby enable others skilled in the art to best utilize the invention and various embodiments with various modifications as are suited to the particular use contemplated.

What is claimed is:

1. A bracket assembly for a surgical robotic system, the bracket assembly comprising:
   a bracket having a first side defining a mounting interface and a second side defining an out of plane portion dimensioned for insertion within a cable opening of an auxiliary video cart; and
   a bracket securing member having an engaging member dimensioned to slidably engage the out of plane portion and a plate dimensioned to support the engaging member and secure the bracket to the auxiliary video cart.

2. The bracket assembly of claim 1 wherein the first side and the second side extend from a distal end to a proximal end of a rectangular base portion of the bracket, the out of plane portion is near the distal end and the mounting interface is near the proximal end.

3. The bracket assembly of claim 1 wherein the mounting interface comprises a recessed region and a pair of slots along opposing sides of the recessed region that are operable to receive a mounting portion of an adapter coupled to a digital hub.

4. The bracket assembly of claim 3 wherein the pair of slots are formed by a pair of tabs that overlap the recessed region and are dimensioned to retain the mounting portion to secure an auxiliary device to the auxiliary video cart.

5. The bracket assembly of claim 1 wherein the out of plane portion comprises an elongated shape that is complimentary to a shape of the cable opening of the auxiliary video cart.

6. The bracket assembly of claim 1 wherein the out of plane portion comprises a sidewall extending from the second side and a slot formed through the sidewall.

7. The bracket assembly of claim 6 wherein the plate comprises a planar portion partially surrounded by a rim and the engaging member comprises a tab extending from the rim and dimensioned for insertion within the slot.

8. The bracket assembly of claim 7 wherein the tab is spaced a distance from the planar portion and operable to slide into the slot in a direction parallel to a plane of the second side.

9. The bracket assembly of claim 1 wherein each of the out of plane portion and the plate comprise at least one screw hole that align with one another and are operable to receive at least one wing nut for securing the bracket and the bracket securing member to the auxiliary video cart.

10. A bracket assembly kit for a surgical robotic system, the bracket assembly kit comprising:
   a bracket having a first side defining a mounting interface for a mounting bracket coupled to an auxiliary device and a second side having an out of plane portion formed by a sidewall comprising a slot formed therein;

a bracket securing member having an engaging member dimensioned to slidably engage the slot formed by the sidewall of the out of plane portion; and a pair of fasteners operable for insertion through the bracket and the bracket securing member to secure the bracket and the bracket securing member to an existing cable opening of a support structure.

11. The bracket assembly kit of claim 10 wherein the bracket comprises a rectangular shape having a distal end and a proximal end, and the out of plane portion is closer to the distal end than the engaging member.

12. The bracket assembly kit of claim 10 wherein the mounting interface comprises a first tab and a second tab that are arranged along opposing sides of a recessed region, and the first tab and the second tab are dimensioned to receive a plate portion of an adapter coupled to the auxiliary device.

13. The bracket assembly kit of claim 10 wherein the sidewall of the out of plane portion extends to a planar top surface having a length dimension greater than a width dimension.

14. The bracket assembly kit of claim 13 wherein the planar top surface comprises a racetrack shape dimensioned for insertion within the existing cable opening of the support structure.

15. The bracket assembly kit of claim 10 wherein the slot extends through the sidewall in a direction parallel to a plane of the second side.

16. The bracket assembly kit of claim 10 wherein the bracket securing member comprises a planar portion partially surrounded by a rim that matches a perimeter of the out of plane portion and provides a receiving space for the out of plane portion.

17. The bracket assembly kit of claim 16 wherein the engaging member comprises a tab extending from the rim.

18. The bracket assembly kit of claim 17 wherein the tab comprises a thickness that is less than a thickness of the rim and is spaced a distance from the planar portion such that the tab is operable to slide into the slot formed in the out of plane portion.

19. The bracket assembly kit of claim 10 wherein the pair of fasteners comprise at least one wing nut operable for insertion through a screw hole in the bracket and bracket securing member.

20. The bracket assembly kit of claim 10 wherein the support structure comprises an auxiliary video cart and the auxiliary device comprises a digital hub.

\* \* \* \* \*